United States Patent [19]

Muller et al.

[11] Patent Number: 5,703,098
[45] Date of Patent: Dec. 30, 1997

[54] IMMUNOTHERAPEUTIC IMIDES/AMIDES

[75] Inventors: George W. Muller, Bridgewater; Mary Shire, North Plainfield; David I. Stirling, Branchburg, all of N.J.

[73] Assignee: Celgene Corporation, Warren, N.J.

[21] Appl. No.: 759,788

[22] Filed: Dec. 3, 1996

Related U.S. Application Data

[63] Continuation-in-part of Ser. No. 366,667, Dec. 30, 1994, abandoned.

[51] Int. Cl.$^6$ .......................... A61K 31/44; C07D 209/48
[52] U.S. Cl. .................. 514/339; 514/417; 546/277.1; 548/476
[58] Field of Search ........................ 514/339, 417; 546/277.1; 548/476

[56] References Cited

PUBLICATIONS

F. Bachelerie et al. (Apr. 25, 1991) *Nature*, vol. 350, pp. 709–712.
Debajit K. Biswas et al. (1993) *Journal of Acquired Immune Deficiency Syndrome*, vol. 6, pp. 778–786.
Ghassan S. Dbaibo et al. (Aug. 25, 1993) *The Journal of Biological Chemistry*, vol. 265 (24), pp. 17762–17766.
Elia J. Duh et al. (Aug. 1989) *Proc. Natl. Acad. Sci. USA*, vol. 86, pp. 5974–5978.
Alexander N. Shakhov et al. (Jan. 1990) *J. Exp. Med.*, vol. 171, pp. 35–47.
Frank J. T. Staal et al. (Dec. 1990) *Proc. Natl. Acad. Sci. USA*, vol. 87, pp. 9943–9947.
Yuichiro J. Suzuki, et al. (Dec. 30, 1992) *Biochemical and Biophysical Research Communications*, vol. 189 (3), pp. 1709–1715.
Yuichiro J. Suzuki, et al. (May 28, 1993) *Biochemical and Biophysical Research Communications*, vol. 193 (1), pp. 277–283.
Yuichiro J. Suzuki et al. (Nov. 1993) *Biochemistry and Molecular Biology International*, vol. 31(4), pp. 693–700.

*Primary Examiner*—Floyd D. Higel
*Attorney, Agent, or Firm*—Mathews, Collins, Shepherd & Gould, P.A.

[57] ABSTRACT

Imide/amide ethers and alcohols are inhibitors of cytokines including tumor necrosis factor α and can be used to combat cachexia, endotoxic shock, arthritis, asthma, and retrovirus replication. A typical embodiment is 3-Phthalimido-3-(3', 4'-dimethoxyphenyl)propan-1-ol.

20 Claims, No Drawings

IMMUNOTHERAPEUTIC IMIDES/AMIDES

This application is a continuation-in-part of U.S. application Ser. No. 08/366,667, filed Dec. 30, 1994, now abandoned.

BACKGROUND OF THE INVENTION

The present invention relates to a method of reducing levels of TNFα and inhibiting phosphodiesterase in a mammal and to compounds and compositions useful therein.

TNFα, or tumor necrosis factor α, is a cytokine which is released primarily by mononuclear phagocytes in response to various immunostimulators. When administered to animals or humans it causes inflammation, fever, cardiovascular effects, hemorrhage, coagulation and acute phase responses similar to those seen during acute infections and shock states.

Excessive or unregulated TNFα production has been implicated in a number of disease conditions. These include endotoxemia and/or toxic shock syndrome {Tracey et al., Nature 330, 662–664 (1987) and Hinshaw et al., Circ. Shock 30, 279–292 (1990)}; cachexia {Dezube et al., Lancet, 335(8690), 662 (1990)}; and Adult Respiratory Distress Syndrome where TNFα concentration in excess of 12,000 pg/milliliter have been detected in pulmonary aspirates from ARDS patients {Millar et al., Lancet 2(8665), 712–714 (1989)}. Systemic infusion of recombinant TNFα also resulted in changes typically seen in ARDS {Ferrai-Baliviera et al., Arch. Surg. 124(12), 1400–1405 (1989)}.

TNFα appears to be involved in bone resorption diseases, including arthritis where it has been determined that when activated, leukocytes will produce a bone-resorbing activity, and data suggest that TNFα contributes to this activity. {Bertolini et al., Nature 319, 516–518 (1986) and Johnson et al., Endocrinology 124(3), 1424–1427 (1989).} It has been determined that TNFα stimulates bone resorption and inhibits bone formation in vitro and in vivo through stimulation of osteoclast formation and activation combined with inhibition of osteoblast function. Although TNFα may be involved in many bone resorption diseases, including arthritis, the most compelling link with disease is the association between production of TNFα by tumor or host tissues and malignancy associated hypercalcemia {Calci. Tissue Int. (US) 46(Suppl.), S3–10 (1990)}. In Graft versus Host Reaction, increased serum TNFα levels have been associated with major complication following acute allogenic bone marrow transplants {Holier et al., Blood, 75(4), 1011–1016 (1990)}.

Cerebral malaria is a lethal hyperacute neurological syndrome associated with high blood levels of TNFα and the most severe complication occurring in malaria patients. Levels of serum TNFα correlated directly with the severity of disease and the prognosis in patients with acute malaria attacks {Grau et at., N. Engl. J. Med. 320(24), 1586–1591 (1989)}.

TNFα also plays a role in the area of chronic pulmonary inflammatory diseases. The deposition of silica particles leads to silicosis, a disease of progressive respiratory failure caused by a fibrotic reaction. Antibody to TNFα completely blocked the silica-induced lung fibrosis in mice {Pignet et al., Nature, 344:245–247 (1990)}. High levels of TNFα production (in the serum and in isolated macrophages) have been demonstrated in animal models of silica and asbestos induced fibrosis {Bissonnette et al., Inflammation 13(3), 329–339 (1989)}. Alveolar macrophages from pulmonary sarcoidosis patients have also been found to spontaneously release massive quantities of TNFα as compared with macrophages from normal donors {Baughman et al., J. Lab. Clin. Med. 115(1), 36–42 (1990)}.

TNFα is also implicated in the inflammatory response which follows reperfusion, called reperfusion injury, and is a major cause of tissue damage after loss of blood flow {Vedder et at., PNAS 87, 2643–2646 (1990)}. TNFα also alters the properties of endothelial cells and has various pro-coagulant activities, such as producing an increase in tissue factor pro-coagulant activity and suppression of the anticoagulant protein C pathway as well as down-regulating the expression of thrombomodulin {Sherry et al., J. Cell Biol. 107, 1269–1277 (1988)}. TNFα has pro-inflammatory activities which together with its early production (during the initial stage of an inflammatory event) make it a likely mediator of tissue injury in several important disorders including but not limited to, myocardial infarction, stroke and circulatory shock. Of specific importance may be TNFα-induced expression of adhesion molecules, such as intercellular adhesion molecule (ICAM) or endothelial leukocyte adhesion molecule (ELAM) on endothelial cells {Munro et al., Am. J. Path. 135(1), 121–132 (1989)}.

Moreover, it now is known that TNFα is a potent activator of retrovirus replication including activation of HIV-1. {Duh et al., Proc. Nat. Acad. Sci. 86, 5974–5978 (1989); Poll et al., Proc. Nat. Acad Sci. 87, 782–785 (1990); Monto et at., Blood 79, 2670 (1990); Clouse et al., J. Immunol. 142, 431–438 (1989); Poll et at., AIDS Res. Hum. Retrovirus, 191–197 (1992)}. AIDS results from the infection of T lymphocytes with Human Immunodeficiency Virus (HIV). At least three types or strains of HIV have been identified, i.e., HIV-1, HIV-2 and HIV-3. As a consequence of HIV infection, T-cell mediated immunity is impaired and infected individuals manifest severe opportunistic infections and/or unusual neoplasms. HIV entry into the T lymphocyte requires T lymphocyte activation. Other viruses, such as HIV-1, HIV-2 infect T lymphocytes after T cell activation and such virus protein expression and/or replication is mediated or maintained by such T cell activation. Once an activated T lymphocyte is infected with HIV, the T lymphocyte must continue to be maintained in an activated state to permit HIV gene expression and/or HIV replication. Cytokines, specifically TNFα, are implicated in activated T-cell mediated HIV protein expression and/or virus replication by playing a role in maintaining T lymphocyte activation. Therefore, interference with cytokine activity such as by prevention or inhibition of cytokine production, notably TNFα, in an HIV-infected individual aids in limiting the maintenance of T lymphocyte caused by HIV infection.

Monocytes, macrophages, and related cells, such as kupffer and glial cells, have also been implicated in maintenance of the HIV infection. These cells, like T cells, are targets for viral replication and the level of viral replication is dependent upon the activation state of the cells. {Rosenberg et al., The Immunopathogenesis of HIV Infection, Advances in Immunology, 57 (1989)}. Cytokines, such as TNFα, have been shown to activate HIV replication in monocytes and/or macrophages {Poli et al. Proc. Natl. Acad Sci., 87, 782–784 (1990)}, therefore, prevention or inhibition of cytokine production or activity aids in limiting HIV progression as stated above for T cells. Additional studies have identified TNFα as a common factor in the activation of HIV in vitro and has provided a clear mechanism of action via a nuclear regulatory protein found in the cytoplasm of cells (Osborn, et al., PNAS 86, 2336–2340). This evidence suggests that a reduction of TNFα synthesis may have an antiviral effect in HIV infections, by reducing the transcription and thus virus production.

HIV viral replication of latent HIV in T cell and macrophage lines can be induced by TNFα {Folks et al., *PNAS* 86, 2365–2368 (1989)}. A molecular mechanism for the virus inducing activity is suggested by TNFα's ability to activate a gene regulatory protein (NFκB) found in the cytoplasm of cells, which promotes HIV replication through binding to a viral regulatory gene sequence (LTR) {Osborn et al., *PNAS* 86, 2336–2340 (1989)}. TNFα in AIDS and cancer associated cachexia is suggested by elevated serum TNFα and high levels of spontaneous TNFα production in peripheral blood monocytes from patients {Wright et al. *J. Immunol.* 141(1), 99–104 (1988)}. {Eur J. Gastroen Hepat, 6(9), 821–829 (1994)}. {J. Exp. Med., 1121–1227 (1988)}.

TNFα has been implicated in various roles with other viral infections, such as the cytomegalia virus (CMV), influenza virus, adenovirus, and the herpes family of viruses for similar reasons as those noted.

Preventing or inhibiting the production or action of TNFα is, therefore, predicted to be a potent therapeutic strategy for many inflammatory, infectious, immunological or malignant diseases. These include but are not restricted to septic shock, sepsis, endotoxic shock, hemodynamic shock and sepsis syndrome, post ischemic reperfusion injury, malaria, mycobacterial infection, meningitis, psoriasis, congestive heart failure, fibrotic disease, cachexia, graft rejection, cancer, autoimmune disease, opportunistic infections in AIDS, rheumatoid arthritis, rheumatoid spondylitis, osteoarthritis, other arthritic conditions, inflammatory bowel disease, Crohn's disease, ulcerative colitis, multiple sclerosis, systemic lupus erythrematosis, ENL in leprosy, asthma, radiation damage, and hyperoxic alveolar injury. Efforts directed to the suppression of the effects of TNFα have ranged from the utilization of steroids such as dexamethasone and prednisolone to the use of both polyclonal and monoclonal antibodies {Beutler et al., *Science* 234, 470–474 ( 1985); WO 92/11383 }. (Clinical and Experimental Rheumatology 1993, 11 (Suppl. 8), 5173–5175). (PNAS 1992, 89, 9784– 88). (Annals of the Rheumatic Diseases 1990, 49, 480–486).

The nuclear factor κB (NFκB) is a pleiotropic transcriptional activator (Lenardo, et al. Cell 1989, 58, 227–29). NFκB has been implicated as a transcriptional activator in a variety of disease and inflammatory states and is thought to regulate cytokine levels including but not limited to TNFα and also to be an activator of HIV transcription (Dbaibo, et al. J. Biol. Chem. 1993, 17762–66; Duh et al. Proc. Natl. Acad. Sci. 1989, 86, 5974–78; Bachelerie et al. Nature 1991, 350, 709–12; Boswas et al. J. Acquired Immune Deficiency Syndrome 1993, 6, 778–786; Suzuki et al. Biochem. And Biophys. Res. Comm. 1993, 193, 277–83; Suzuki et al. Biochem. And Biophys. Res Comm. 1992, 189, 1709–15; Suzuki et al. Biochem. Mol. Bio. Int. 1993, 31(4), 693–700; Shakhov et al. 1990, 171, 35–47; and Staal et al. Proc. Natl. Acad. Sci. U.S.A. 1990, 87, 9943–47). Thus, inhibition of NFκB binding can regulate transcription of cytokine gene(s) and through this modulation and other mechanisms be useful in the inhibition of a multitude of disease states. The compounds claimed in this patent can inhibit the action of NFκB in the nucleus and thus are useful in the treatment of a variety of diseases including but not limited to rheumatoid arthritis, rheumatoid spondylitis, osteoarthritis, other arthritic conditions, septic shock, septis, endotoxic shock, graft versus host disease, wasting, Crohn's disease, ulcerative colitis, multiple sclerosis, systemic lupus erythrematosis, ENL in leprosy, HIV, AIDS, and opportunistic infections in AIDS.

TNFα and NFκB levels are influenced by a reciprocal feedback loop. As noted above, the compounds of the present invention affect the levels of both TNFα and NFκB. It is not known at this time, however, how the compounds of the present invention regulate the levels of TNFα, NFκB, or both.

Many cellular functions can be mediated by levels of adenosine 3',5'-cyclic monophosphate(cAMP). Such cellular functions can contribute to inflammatory conditions and diseases including asthma, inflammation, and other conditions (Lowe and Cheng, *Drugs of the Future*, 17(9), 799–807, 1992). It has been shown that the elevation of cAMP in inflammatory leukocytes inhibits their activation and the subsequent release of inflammatory mediators. Increased levels of cAMP also leads to the relaxation of airway smooth muscle.

The primary cellular mechanism for the inactivation of cAMP is the breakdown of cAMP by a family of isoenzymes referred to as cyclic nucleotide phosphodiesterases (PDE) (Beavo and Reitsnyder, *Trends in Pharm.*, 11, 150–155, 1990). There are seven known members of the family of PDEs. It is recognized, for example, that the inhibition of PDE type IV is particularly effective in both the inhibition of inflammatory mediator release and the relaxation of airway smooth muscle (Verghese, et al., *Journal of Pharmacology and Experimental Therapeutics*, 272(3), 1313–1320, 1995). Thus, compounds that inhibit PDE IV specifically, would exhibit the desirable inhibition of inflammation and relaxation of airway smooth muscle with a minimum of unwanted side effects, such as carrio-vascular or anti-platelet effects. Currently used PDE IV inhibitors lack the selective action at acceptable therapeutic doses.

The compounds of the present invention are useful in the inhibition of phosphodiesterases, particularly PDE III and PDE IV, and in the treatment of disease states mediated thereby.

DETAILED DESCRIPTION

The present invention is based on the discovery that a class of non-polypeptide imides/amides more fully described herein appear to inhibit the action of TNFα.

The present invention pertains to compounds of the formula:

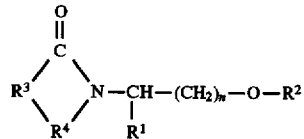

in which R¹ is (i) straight, branched, or cyclic, substituted or unsubstituted alkyl of 1 to 12 carbon atoms, (ii) phenyl or phenyl substituted with one or more substituents, where each substituent is selected independently of the other from nitro, cyano, trifluoromethyl, carbethoxy, carbomethoxy, carbopropoxy, acetyl, carbamoyl, acetoxy, carboxy, hydroxy, amino, acylamino, alkylamino, di(alkyl)amino, alkyl of 1 to 10 carbon atoms, cycloalkyl of 3 to 10 carbon atoms, bicycloalkyl of 5 to 12 carbon atoms, alkoxy of 1 to 10 carbon atoms, cycloalkoxy of 3 to 10 carbon atoms, bicycloalkoxy of 5 to 12 carbon atoms, or halo;

R² is —H, alkyl of 1 to 8 carbon atoms, benzyl, pyridylmethyl, or alkoxymethyl;

R³ is i) ethylene, ii) vinylene, iii) a branched alkylene of 3 to 10 carbon atoms, iv) a branched alkenylene of 3 to 10 carbon atoms, v) cycloalkylene of 4 to 9 carbon atoms unsubstituted or substituted with 1 or more substituents each selected independently from nitro, cyano, trifluoromethyl, carbethoxy, carbomethoxy, carbopropoxy, acetyl, carbamoyl, acetoxy, carboxy, hydroxy, amino, amino substituted with alkyl of 1 to 6 carbon atoms amino substituted with acyl of 1 to 6 carbon atoms, alkyl of 1 to 10 carbon atoms, alkoxy of 1 to 12 carbon atoms, or halo, vi) cycloalkenylene of 4 to 9 carbon atoms unsubstituted or substituted with 1 or more substituents each selected independently from nitro, cyano, trifluoromethyl, carbethoxy, carbomethoxy, carbopropoxy, acetyl, carbamoyl, acetoxy, carboxy, hydroxy, amino, amino substituted with alkyl of 1 to 6 carbon atoms, amino substituted with acyl of 1 to 6 carbon atoms, alkyl of 1 to 10 carbon atoms, alkoxy of 1 to 12 carbon atoms, or halo, vii) o-phenylene unsubstituted or substituted with 1 or more substituents each selected independently from nitro, cyano, trifluoromethyl, carbethoxy, carbomethoxy, carbopropoxy, acetyl, carbamoyl, acetoxy, carboxy, hydroxy, amino, amino substituted with alkyl of 1 to 6 carbon atoms, amino substituted with acyl of 1 to 6 carbon atoms, alkyl of 1 to 10 carbon atoms, alkoxy of 1 to 12 carbon atoms, or halo, viii) naphthyl, or ix) pyridyl;

$R^4$ is —CX—, —CH$_2$— or —CH$_2$CX—;

X is O or S; and, n is 0, 1, 2, or 3.

A first preferred subclass of Formula II pertains to compounds in which $R^3$ is o-phenylene where:

$R^1$ is 3,4-diethoxyphenyl or 3-ethoxy-4-methoxyphenyl and $R^4$ is —CO—, —CH$_2$— or —CH$_2$CO—.

Typical compounds of this invemion include 3-phthalimido-3-(3',4'-dimethoxyphenyl)propan-1-ol; 2-phthalimido-2-(3',4'-dimethoxyphenyl)ethanol; 3-phthalimido-3-(3',4'-diethoxyphenyl)propan-1-ol; 3-phthalimido-3-(3',4'-dimethoxyphenyl)-1-methoxypropane; 2-phthalimido-2-(3',4'-dimethoxyphenyl)-1-methoxyethane; 3-phthalimido-3-(3',4'-diethoxyphenyl)-1-methoxypropane; 3-phthalimido-3-(3',4'-dimethoxyphenyl)-1-ethoxypropane; 3-phthalimido-3-(3',4'-dimethoxyphenyl)-1-(3-pyridylmethoxy)propane; 3-phthalimido-3-(3',4'-diethoxyphenyl)-1-(3-pyridylmethoxyl)propane; 3-phthalimido-3-napthylpropan-1-ol; 3-phthalimido-3-(3',4'-diethylphenyl)propan-1-ol; 3-phthalimido-3-(3',4'-dipropylphenyl)propan-1-ol; 3-phthalimido-3-(3',4'-diethylphenyl)-1-methoxypropane; 3-phthalimido-3-(3',4'-diethoxyphenyl)-1-ethoxypropane; 3-phthalimido-3-cyclohexyl-1-methoxypropane; 3-phthalimido-3-(3',4'-diethylcyclohexyl)-1-methoxypropane; 3-(1'-oxoisoindolinyl)-3-(3',4'-dimethoxyphenyl)propan-1-ol; 2-(1'-oxoisoindolinyl)-2-(3',4'-dimethoxyphenyl)ethanol; 3-(1'-oxoisoindolinyl)-3-(3',4'-diethoxyphenyl)propan-1-ol; 3-(1'-oxoisoindolinyl-3-(3',4'-dimethoxyphenyl)-1-methoxypropane; 2-(1'-oxoisoindolinyl)-2-(3',4'-dimethoxyphenyl)-1-methoxyethane; 3-(1'-oxoisoindolinyl)-3-(3',4'-diethoxyphenyl)-1-methoxypropane; 3-(1'-oxoisoindolinyl)-3-(3',4'-dimethoxyphenyl)-1-ethoxypropane; 3-(1'-oxoisoindolinyl)-3-(3',4'-dimethoxyphenyl)-1-(3-pyridylmethoxy)propane; 3-(1'-oxoisoindolinyl)-3-(3',4'-diethoxyphenyl)-1-(3-pyridylmethoxyl)propane; 3-(1'-oxoisoindolinyl)-3-napthylpropan-1-ol; 3-(1'-oxoisoindolinyl)-3-(3',4'-diethylphenyl)propan-1-ol; 3-(1'-oxoisoindolinyl)-3-(3',4+-dipropylphenyl)propan-1-ol; 3-(1'-oxoisoindolinyl)-3-(3',4'-diethylphenyl)-1-methoxypropane; 3-(1'-oxoisoindolinyl)-3-(3',4'-diethoxyphenyl)-1-ethoxypropane. 3-phthalimido-3-(3'-ethoxy-4'-methoxyphenyl)propan-1-ol 3-phthalimido-3-(3'-ethoxy-4'-methoxyphenyl)-1-methoxypropane 3-phthalimido-3-(3'-propoxy-4'-methoxyphenyl)propan-1-ol 3-phthalimido-3-(3'-propoxy-4'-methoxyphenyl)-1-methoxypropane 3-phthalimido-3-(3'-cyclopentoxy-4'-methoxyphenyl)propan-1-ol 3-phthalimido-3-(3'-cyclopentoxy-4'-methoxyphenyl)-1-methoxypropane 3-phthalimido-3-(3'-isopropoxy-4'-methoxyphenyl)propan-1-ol 3-phthalimido-3-(3'-isopropoxy-4'-methoxyphenyl)-1-methoxypropane 3-phthalimido-3-(3'-ethoxy-4'-ethylphenyl)propan-1-ol 3-phthalimido-3-(3'-ethoxy-4'-ethylphenyl)-1-methoxypropane 3-(1'-oxoisoindolinyl)-3-(3'-ethoxy-4'-methoxyphenyl)-1-methoxypropane 3-(1'-oxoisoindolinyl)-3-(3'-propoxy-4'-methoxyphenyl)propan-1-ol 3-(1'-oxoisoindolinyl)-3-(3'-propoxy-4'-methoxyphenyl)-1-methoxypropane 3-(1'-oxoisoindolinyl)-3-(3'-cyclopentoxy-4'-methoxyphenyl)propan-1-ol 3-(1'-oxoisoindolinyl)-3-(3'-cyclopentoxy-4'-methoxyphenyl)-1-methoxypropane 3-(1'-oxoisoindolinyl)-3-(3'-isopropoxy-4'-methoxyphenyl)propan-1-ol 3-(1'-oxoisoindolinyl)-3-(3'-isopropoxy-4'-methoxyphenyl)-1-methoxypropane 3-(1'-oxoisoindolinyl)-3-(3'-ethoxy-4'-ethylphenyl)propan-1-ol 3-(1'-oxoisoindolinyl)-3-(3'-ethoxy-4'-ethylphenyl)-1-methoxypropane 3-(3-aminophthalimido)-3-(3'-ethoxy-4'-methoxyphenyl)-1-methoxypropane 3-(3-aminophthalimido)-3-(3'-propoxy-4'-methoxyphenyl)propan-1-ol 3-(3-aminophthalimido)-3-(3'-propoxy-4'-methoxyphenyl)-1-methoxypropane 3-(3-aminophthalimido)-3-(3'-cyclopentoxy-4'-methoxyphenyl)propan-1-ol 3-(3-aminophthalimido)-3-(3'-cyclopentoxy-4'-methoxyphenyl)-1-methoxypropane 3-(3-aminophthalimido)-3-(3'-isopropoxy-4'-methoxyphenyl)propan-1-ol 3-(3-aminophthalimido)-3-(3'-isopropoxy-4'-methoxyphenyl)-1-methoxypmpane 3-(3-aminophthalimido)-3-(3'-ethoxy-4'-ethylphenyl)propan-1-ol 3-(3-aminophthalimido)-3-(3'-ethoxy-4'-ethylphenyl)-1-methoxypropane 3-(3-hydroxyphthalimido)-3-(3'-ethoxy-4'-methoxyphenyl)-1-methoxypropane 3-(3-hydroxyphthalimido)-3-(3'-propoxy-4'-methoxyphenyl)propan-1-ol 3-(3-hydroxyphthalimido)-3-(3'-propoxy-4'-methoxyphenyl)-1-methoxypropane 3-(3-hydroxyphthalimido)-3-(3'-cyclopentoxy-4'-methoxyphenyl)propan-1-ol 3-(3-hydroxyphthalimido)-3-(3'-cyclopentoxy-4'-methoxyphenyl)-1-methoxypropane 3-(3-hydroxyphthalimido)-3-(3'-isopropoxy-4'-methoxyphenyl)propan-1-ol 3-(3-hydroxyphthalimido)-3-(3'-isopropoxy-4'-methoxyphenyl)-1-methoxypropane 3-(3-hydroxyphthalimido)-3-(3'-ethoxy-4'-ethylphenyl)propan-1-ol 3-(3-hydroxyphthalimido)-3-(3'-ethoxy-4'-ethylphenyl)-1-methoxypropane 3-homophthalimido-3-(3'-ethoxy-4'-methoxyphenyl)-1-methoxypropane 3-homophthalimido-3-(3'-propoxy-4'-methoxyphenyl)propan-1-ol 3-homophthalimido-3-(3'-propoxy-4'-methoxyphenyl)-1-methoxypropane 3-homophthalimido-3-(3'-cyclopentoxy-4'-methoxyphenyl)propan-1-ol 3-homophthalimido-3-(3'-cyclopentoxy-4'-methoxyphenyl)-1-methoxypropane 3-homophthalimido-3-(3'-isopropoxy-4'-methoxyphenyl)propan-1-ol 3-homophthalimido-3-(3'-isopropoxy-4'-methoxyphenyl)-1-methoxypropane 3-homophthalimido-3-(3'-ethoxy-4'-ethylphenyl)propan-1-ol 3-homophthalimido-3-(3'-ethoxy-4'-ethylphenyl)-1-methoxypropane 3-(4-aminophthalimido)-3-(3'-ethoxy-4'-methoxyphenyl)-1-methoxypropane 3-(4-aminophthalimido)-3-(3'-propoxy-4'-methoxyphenyl)propan-1-ol 3-(4-aminophthalimido)-3-(3'-propoxy-4'-methoxyphenyl)-1-methoxypropane 3-(4-aminophthalimido)-3-(3'-cyclopentoxy-4'-methoxyphenyl)propan-1-ol 3-(4-aminophthalimido)-3-(3'-cyclopentoxy-4'-methoxyphenyl)-1-methoxypropane 3-(4-aminophthalimido)-3-(3'-isopropoxy-4'-methoxyphenyl)propan-1-ol 3-(4-aminophthalimido)-3-(3'-isopropoxy-4'- methoxyphenyl)-1-methoxypropane 3-(4-aminophthalimido)-3-(3'-ethoxy-4'-ethylphenyl)propan-1-ol 3-(4-aminophthalimido)-3-(3'-ethoxy-4'-ethylphenyl)-1-methoxypropane The term alkyl as used herein denotes a univalent saturated branched or straight hydrocarbon chain. Unless otherwise stated, such chains can contain from 1 to 18 carbon atoms. Representative of such alkyl groups are methyl, ethyl, propyl, isopropyl, butyl, isobutyl, sec-butyl, tert-butyl, pentyl, isopentyl, neopentyl, tert-pentyl, hexyl, isohexyl, heptyl, octyl, nonyl, decyl, undecyl, dodecyl, tridecyl, tetradecyl, pentadecyl, hexadecyl, heptadecyl, octadecyl, and the like. When qualified by "lower", the alkyl group will contain from 1 to 6 carbon atoms. The same carbon content applies to the parent term "alkane" and to derivative terms such as "alkoxy".

The compounds can be used, under the supervision of qualified professionals, to inhibit the undesirable effects of TNFα. The compounds can be administered orally, rectally, or parenterally, alone or in combination with other therapeutic agents including antibiotics, steroids, etc., to a mammal in need of treatment. Oral dosage forms include tablets, capsules, dragees, and similar shaped, compressed pharmaceutical forms. Isotonic saline solutions containing 20–100 milligrams/milliliter can be used for parenteral administration which includes intramuscular, intrathecal, intravenous and intra-arterial routes of administration. Rectal administration can be effected through the use of suppositories formulated from conventional carriers such as cocoa butter.

Dosage regimens must be titrated to the particular indication, the age, weight, and general physical condition of the patient, and the response desired but generally doses will be from about 1 to about 500 milligrams/day as needed in single or multiple daily administration. In general, an initial treatment regimen can be copied from that known to be effective in interfering with TNFα activity for other TNFα mediated disease states by the compounds of the present invention. Treated individuals will be regularly checked for T cell numbers and T4/T8 ratios and/or measures of viremia such as levels of reverse transcriptase or viral proteins, and/or for progression of cytokine-mediated disease associated problems such as cachexia or muscle degeneration. If no effect is found following the normal treatment regimen, then the amount of cytokine activity interfering agent administered is increased, e.g., by fifty percent a week.

The compounds of the present invention also can be used topically in the treatment or prophylaxis of topical disease states mediated or exacerbated by excessive TNFα production, respectively, such as viral infections, such as those caused by the herpes viruses, or viral conjunctivitis, etc.

The compounds also can be used in the veterinary treatment of mammals other than humans in need of prevention or inhibition of TNFα production. TNFα mediated diseases for treatment, therapeutically or prophylactically, in animals include disease states such as those noted above, but in particular viral infections. Examples include feline immunodeficiency virus, equine infectious anaemia virus, caprine arthritis virus, visna virus, and maedi virus, as well as other lentiviruses.

Certain of these compounds possess centers of chirality and can exist as optical isomers. Both the racemates of these isomers and the individual isomers themselves, as well as diastereomers when there are two chiral centers, are within the scope of the present invention. The racemates can be used as such or can be separated into their individual isomers mechanically as by chromatography using a chiral absorbant. Alternatively, the individual isomers can be prepared in chiral form or separated chemically from a mixture by forming salts with a chiral acid, such as the individual enantiomers of 10-camphorsulfonic acid, camphoric acid, alpha-bromocamphoric acid, methoxyacetic acid, tartaric acid, diacetyltartaric acid, malic acid, pyrrolidone-5-carboxylic acid, and the like, and then freeing one or both of the resolved bases, optionally repeating the process, so as to obtain either or both substantially free of the other; i.e., in a form having an optical purity of >95%.

Prevention or inhibition of production of TNFα by these compounds can be conveniently assayed using anti-TNFα antibodies. For example, plates (Nunc Immunoplates, Roskilde, DK) are treated with 5 μg/milliliter of purified rabbit anti-TNFα antibodies at 4° C. for 12 to 14 hours. The plates then are blocked for 2 hours at 25° C. with PBS/0.05% Tween containing 5 milligrams/milliliter BSA. After washing, 100 μL of unknowns as well as controls are applied and the plates incubated at 4° C. for 12 to 14 hours. The plates are washed and assayed with a conjugate of peroxidase (horseradish) and mouse anti-TNFα monoclonal antibodies, and the color developed with o-phenylenediamine in phosphate-citrate buffer containing 0.012% hydrogen peroxide and read at 492 nm.

The compounds can be prepared using methods which are known in general for the preparation of imides. A preferred general reaction scheme includes the reaction of a substituted amine with an appropriate anhydride. Other synthetic methods known in the art may be used, for example, phthalimido compounds are made by reacting the substituted amine with either phthalic anhydride, N-carbethoxyphthalimide, or phthalic dicarboxaldehyde as illustrated by the formulas:

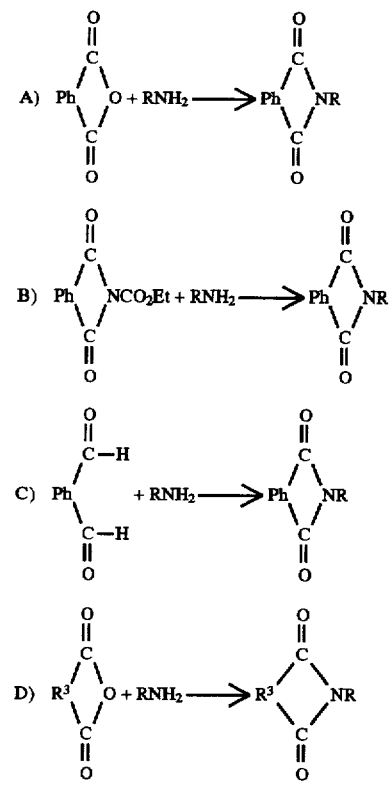

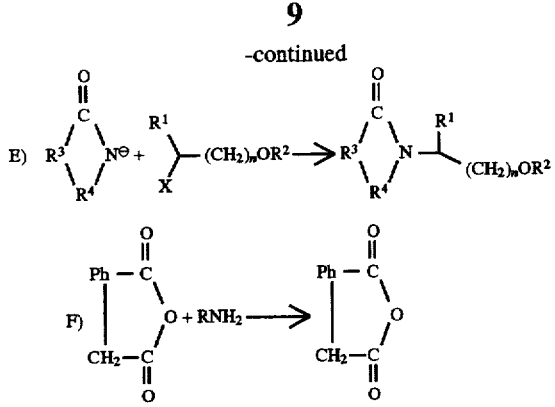

The following examples will serve to further typify the nature of this invention but should not be construed as a limitation in the scope thereof, which scope is defined solely by the appended claims.

EXAMPLE 1

3-Amino-3-(3',4'-dimethoxyphenyl)propionic acid

A stirred suspension of 3,4-dimethoxybenzaldehyde (131 grams, 788 mmol) and ammonium acetate (121.5 grams, 1576 mmol) in ethanol (95%, 400 mL) was heated to 45°–50° C. resulting in an orange solution. To this solution was added malonic acid (82.0 grams, 788 mmol) and the solution was refluxed overnight. A white solid precipitated on heating, the slurry was allowed to cool to room temperature and was filtered. The solid was washed with ethanol, air dried, and dried in vacuo (60° C.,<1 mm) to afford 3-amino-3-(3',4'-dimethoxyphenyl)propionic acid as a white solid, ( 100.14 grams, 56% yield), no further purification was carded out: mp 208.0°–210.0° C.; $^1$H NMR (D$_2$O/NaOD/TSP)$\delta$7.08–6.91 (m, 3H), 4.22 (t, J=7 Hz, 1H), 3.87 (s, 3H), 3.83 (s, 3H), 2.55 (dd, J=2, 7Hz, 2H); $^{13}$C NMR(D$_2$O/NaOD/TSP)$\delta$182.9, 150.8, 149.8, 140.7, 121.6, 114.6, 112.8, 58.6, 55.4, 49.8.

EXAMPLE 2

Methyl 3-amino-3-(3',4'-dimethoxyphenyl) propionate

To a stirred suspension of 3-amino-3-(3',4'-dimethoxyphenyl)propionic acid (70.1 grams, 312 mmol) in methanol (400 mL) at 0° C., was added acetyl chloride (47.6 mL, 667 mmol) dropwise. After an additional 15 minutes, the ice-water bath was removed. The resulting clear solution was stirred at room temperature for 2 hours. The system was opened and the solvent was blown off with N$_2$ overnight. To the solid was added methanol (50 mL) and ether (300 mL). The resulting suspension was stirred at room temperature for 1 hour. The suspension was filtered and the solid was washed with ether (100 mL). The solid was dissolved in a mixture of sodium carbonate (200 mL, sat), water (200 mL), and methylene chloride (250 mL). The organic layer was separated. The aqueous layer was extracted with methylene chloride (3×250 mL). The combined organic layers were dried over magnesium sulfate. Removal of solvent gave methyl 3-amino-3-(3',4'-dimethoxyphenyl)propionate as an oil (60.2 grams, 81% yield): $^1$H NMR (CDCl$_3$)$\delta$1.77 (s, 2H, NH$_2$), 2.65 (d, J=7 Hz, 2H, CH$_2$), 3.68 (s, 3H, CH$_3$), 3.87 (s, 3H, CH$_3$), 3.89 (s, 3H, CH$_3$), 4.39 (t, J=Hz, 1H, CH), 6.81–6.93 (m, 3H, Ar); $^{13}$C NMR (CDCl$_3$)$\delta$44.00, 51.48, 52.18, 55.72, 55.76, 109.20, 111.02, 118.02, 137.21, 148.11, 148.93, 172.34; Anal. Calcd for C$_{12}$H$_{17}$NO$_4$0.1 H$_2$OC, 59.19; H, 7.19; N, 5.81. Found: C, 59.38; H, 7.09; N, 5.91.

EXAMPLE 3

3-Amino-3-(3',4'-dimethoxyphenyl)-propan-1-ol

A solution of 3-amino-3-(3',4'-dimethoxyphenyl)-propionate (4.12 grams, 17.2 mmol) in methanol (50 milliliters) was slowly added to stirred sodium borohydride (6.51 grams, 17.2 mmol). After the initial effervescence had ceased the mixture was refluxed for 1 hour. Reaction progress was monitored by TLC (20% ethyl acetate/hexane, uv) and was complete after 1 hour. The reaction mixture was allowed to cool and then 20 milliliters of water was added. The methanol was removed in vacuo resulting in the formation of a gum which was extracted into methylene chloride (3×20 milliliters). The combined extracts were dried over magnesium sulfate and concentrated to afford an oil which was refrigerated. A waxy solid formed which was dried in vacuo (60° C.,<1 mm) to afford 3.30 g (86%) of the product as a white solid. $^1$H NMR (CDCl$_{13}$)$\delta$6.91–6.78(m, 3H), 4.15–4.04(m, 1H), 3.89(s, 3H), 3.88(s, 3H), 3.84–3.71 (s, 2H), 3.91–2.45(broad m, 1H), 1.95–1.78(m, 2H).

EXAMPLE 4

3-Amino-3-(3',4'-dimethoxyphenyl)-1-propanol

To a stirred solid of sodium borohydride (94.18 grams, 2.49 mol) at 0° C., was added methanol (50 mL). To this mixture at 0° C. was added a solution of methyl 3-amino-3-(3',4'-dimethoxyphenyl)propionate (59.5 grams, 249 mmol) in methanol (950 mL) over 1 hour. The mixture was stirred in that ice-water bath until the temperature of the reaction mixture stayed at 35° C. or lower for 30 minutes. (Caution: If the ice-water bath was removed too early, a highly exothermic reaction may occur.) The water bath was then removed and the solution was refluxed for 16 hours. The solution was allowed to cool to room temperature. To the solution was added water (300 mL), followed by methylene chloride (250 mL) at 0° C. The resulting suspension was filtered. Half of the filtrate was removed in vacuo. The resulting solution was dissolved in methylene chloride (500 mL) and water (300 mL). The organic layer was separated. The aqueous layer was extracted with methylene chloride (3×500 mL). The combined organic layers were washed with brine (100 mL), and dried over magnesium sulfate. Removal of solvent gave an oil. The resulting oil was dried in vacuo to afford 3-amino-3-(3',4'-dimethoxyphenyl)-1-propanol as a white solid (42.15 grams, 80% yield): mp 63.5°–65.5° C.; $^1$H NMR (CDCl$_3$)$\delta$6.91–6.78(m, 3H), 4.15–4.04(m, 1H), 3.89(s, 3H), 3.88(s, 3H), 3.84–3.71(s, 2H), 2.91–2.45(m, 1H), 1.95–1.78(m, 2H); Anal Calcd for C$_{11}$H$_{17}$NO$_3$:C, 62.54; H, 8.11; N, 6.63. Found: C, 62.01; H, 7.80; N, 6.49.

EXAMPLE 5

3-Phthalimido-3-(3',4'-dimethoxyphenyl)propan-1-ol

A mixture of 3-amino-3-(3',4'-dimethoxyphenyl)-propan-1-ol (1.11 grams, 5 mmol) and phthalic anhydride (0.74 grams, 5 mmol) were melted together and stirred for 5 minutes. After cooling, a green/yellow glassy semi solid formed which was stirred in ether to afford 1.62 g (95%) of crude product as a white solid. The crude product was purified by flash chromatography (silica gel, 40% ethyl acetate/methylene chloride) to afford 1.25 grams (73%) of product as a white solid. $^1$H NMR (CDCl$_3$)δ7.85–7.63 (m, 4H), 7.18–7.07 (m , 2H), 6.86–6.76 (m, 1H), 5.62–5.49(m, 1H), 3.88 (s, 3H), 3.85 (s, 3H), 3.79–3.63 (m, 2H), 2.89–2.71 (m, 1H), 2.64–2.47 (m, 1H), 1.87–1.73 (br m, 1H). $^{13}$C NMR (CDCl$_3$)δ168.5, 148.8, 148.6, 133.9, 131.8, 131.7, 123.2, 120.7, 111.6, 110.8, 59.8, 55.0, 55.8, 51.4, 33.9. Anal. Calcd. for C$_{19}$H$_{19}$NO$_5$. Theoretical: C, 66.85; H, 5.61 ;N, 4.10. Found: C, 66.70; H, 5.60; N, 4.06. HPLC 100%.

EXAMPLE 6

3-Amino-3-(3'-ethoxy-4'-methoxyphenyl)propionic acid

A stirred mixture of 3-ethoxy-4-methoxybenzaldehyde (119.5 grams, 664 mmol) and ammonium acetate (148.3 grams, 1.92 mol) in ethanol (300 mL, 95%) was heated at 45° C. To the mixture was added malonic acid (69 grams, 664 mmol), followed by ethanol (100 mL, 95%). The mixture was refluxed for 18 hours. The mixture was cooled to room temperature and was stirred for 2 hours. The suspension was filtered and the solid was washed with cold ethanol (5×50 mL) to give 3-amino-3-(3'-ethoxy-4'-methoxyphenyl)propionic acid as a white solid, which was dried in a vacuum oven overnight, (94.75 grams, 60% yield): mp, 224.0°–225.5° C.; $^1$H NMR (D$_2$O/NaOD)δ1.41 (t, J=7 Hz, 3H, CH$_3$), 2.52–2.56 (m, 2H, CH$_2$), 3.83 (s, 3H, CH$_2$), 4.14 (q, J=7 Hz, 2H, CH$_2$), 4.19 (t, J=7 Hz, 1H, NCH), 6.98–7.04 (m, 3H, Ar); $^{13}$C NMR (D$_2$O/NaOD)δ16.75, 49.81, 55.45, 58.46, 67.63, 114.17, 114.71, 121.76, 140.69, 149.91, 150.09, 182.97; Anal. Calcd for C$_{12}$H$_{17}$NO$_4$: C, 60.24; H, 7.16; N, 5.85. Found: C, 60.21; H, 7.12;N, 5.88.

EXAMPLE 7

Methyl 3-amino-3-(3'-ethoxy-4'-methoxyphenyl) propionate

To a stirred suspension of 3-amino-3-(3'-ethoxy-4'-methoxyphenyl)propionic acid (89.47 grams, 374.4 mmol) in methanol (500 mL) at 0° C., was added acetyl chloride (54 mL, 757 mmol) dropwise. After 15 minutes, the ice-water bath was removed. The resulting clear solution was stirred at room temperature for 2 hours. The system was opened and the solvent was blown off with N$_2$ overnight. To the solid was added methanol (50 mL) and ether (300 mL). The resulting suspension was stirred at room temperature for 1 hour. The suspension was filtered and the solid was washed with ether (100 mL). The solid was dissolved in a mixture of sat aqueous sodium carbonate (200 mL), water (200 mL), and methylene chloride (250 mL). The organic layer was separated. The aqueous layer was extracted with methylene chloride (3×250 mL). The combined organic layers were dried over magnesium sulfate. Removal of solvent gave methyl 3-amino-3-(3'-cyclopentoxy-4'-methoxyphenyl) propionate as an oil (80.84 grams, 85% yield): $^1$H NMR (CDCl$_3$)δ1.46 (t, d=7 Hz, 3H, CH$_3$), 1.75 (s, 2H, NH$_2$), 2.64 (d, d=7 Hz, 2H, CH$_2$), 3.68 (s, 3H, CH$_3$), 3.86 (s, 3H, CH$_3$), 4.10 (q, d=7 Hz, 2H, CH$_2$), 5.36 (t, d=7 Hz, 1H, NCH), 6.80–6.91 (m, 3H, Ar); $^{13}$C NMR (CDCl$_3$)δ14.74, 44.09, 51.55, 52.23, 55.91, 64.23, 110.77, 111.39, 118.07, 137.21, 148.31,148.49, 172.44.

EXAMPLE 8

3-Amino-3-(3'-ethoxy-4'-methoxyphenyl)-1-propanol

To a stirred solid of sodium borohydride (121 grams, 3.19 mol) at 0° C., was added methanol (50 mL). To this mixture at 0° C. was added a solution of methyl 3-amino-3-(3'-ethoxy-4'-methoxyphenyl)propionate (80.84 grams, 319.5 mmol) in methanol (1500 mL) over 1 hour. The mixture was stirred in that ice-water bath until the temperature of the reaction mixture stayed at 35° C. or lower for 30 minutes. (Early removal of the ice bath may result in a highly exothermic reaction). The water bath was then removed and the solution was refluxed for 16 hours. The solution was allowed to cool to room temperature. To the solution was added water (300 mL), followed by methylene chloride (250 mL) at 0° C. The resulting suspension was filtered. Half of the filtrate was removed in vacuo. The resulting solution was dissolved in methylene chloride (500 mL) and water (300 mL). The organic layer was separated. The aqueous layer was extracted with methylene chloride (3×500 mL). The combined organic layers were washed with brine (100 mL), and dried over magnesium sulfate. Removal of solvent gave an oil. The resulting oil was dried in vacuo to afford 3-amino-3-(3'-ethoxy-4'-methoxyphenyl)-1-propanol as a white solid (53 grams, 74% yield): $^1$H NMR (CDCl$_3$)δ1.47 (t, J=6.8 Hz, 3H, CH$_3$), 1.84–1.90 (m, 2H, CH$_2$), 2.58 (br s, 3H, NH$_2$, OH), 3.78 (t, J=5.5 Hz, 2H, OCH$_2$), 3.86 (s, 3H, CH$_2$), 4.04–4.15 (m, 3H, CH$_2$, NCH), 6.84 (s, 3H, Ar); $^{13}$C NMR (CDCl$_3$)δ14.74, 39.78, 55.84, 55.91, 61.86, 64.28, 110.55, 111.47, 117.58, 138.82, 148.27, 148.32; Anal. Calcd for C$_{12}$H$_{19}$NO$_3$: C, 63.98; H, 8.50; N, 6.22. Found: C, 63.73; H, 8.44; N, 6.14.

EXAMPLE 9

3-(3'-Ethoxy-4'-methoxyphenyl)-3-phthalimido-1-propanol

A mixture of 3-amino-3-(3'-ethoxy-4'-methoxyphenyl)-1-propanol (8.4 grams, 37.3 mmol) and sodium carbonate (3.95 grams, 37.3 mmol) in acetonitrile and water (40 mL each) was stirred at room temperature for 15 minutes. To the solution was added N-carbethoxyphthalimide (8.18 grams, 37.3 mmol) as solid. After 20 minutes, the acetonitrile was removed under vacuum. The aqueous solution was extracted with methylene chloride (3×50 mL). The combined organic layers were washed with HCl (40 mL, 1N), and dried over magnesium sulfate. Removal of solvent gave a green oil. Ether (25 mL) was added to the oil, then hexane (2 mL) was added. A suspension formed and the solid was filtered to give 3-(3'-ethoxy-4'-methoxyphenyl)-3-phthalimido-1-propanol as a white solid, 1 g. The mother liquor was purified by chromatography (silica gel 500 grams, 10, 15, 20% EtOAc/CH$_2$Cl$_2$) to give 3-(3'-ethoxy-4'-methoxyphenyl)-3-phthalimido-1-propanol as a solid, 2.54 g. Total yield was 3.54 g (27% yield): mp, 112.0°–114.0° C.; $^1$H NMR (CDCl$_3$)δ1.45 (t, J=7 Hz, 3H, CH$_3$), 1.59–1.65 (br s, 1H, OH), 2.49–2.59 (m, 1H, CHH), 2.71–2.83 (m, 1H, CHH), 3.66–3.69 (m, 2H, OCH$_2$), 3.84 (s, 3H, CH$_3$), 4.10 (q, J=7 Hz, 2H, MeCH$_2$), 5.53 (dd, J=6.5, 9.5 Hz, 1H, NCH), 6.81 (d, J=8.2 Hz, 1H, Ar), 7.09–7.27 (m, 2H, Ar), 7.66–7.72 (m, 2H, Ar), 7.76–7.82 (m, 2H, Ar); $^{13}$C NMR (CDCl$_3$) δ14.72, 33.86, 51.46, 55.88, 59.84, 64.34, 111.16, 113.05, 120.68, 123.20, 131.64, 131.86, 133.94, 148.17, 148.97, 168.49; Anal Calcd for C$_{20}$H$_{21}$NO$_5$: C, 67.59; H, 5.96; N, 3.94. Found: C, 65.40; H, 5.81; N, 3.84.

EXAMPLE 10

3-Amino-3-(3-cyclopentyloxy-4-methoxyphenyl) propionic acid

A stirred mixture of 3-cyclopentyloxy-4-methoxybenzaldehyde (54.9 grams, 249 mmol) and ammonium acetate (58.2 grams, 748 mmol) in ethanol (200 mL, 95%) was heated to 45° C. To the yellowish suspension, was added malonic acid (25.9 grams, 249 mmol) as a solid. The mixture was refluxed for 16 h. The mixture was cooled to room temperature. The suspension was filtered and the solid was washed with cold ethanol (200 mL) until the color was removed. The white solid was dried in a vacuum oven (45° C., 1 torr) to afford 3-amino-3-(3'-cyclopentoxy-4'-methoxyphenyl)propionic acid as white solid (41.97 grams, 61% yield): mp, 234.0°–235.0° C.; $^1$H NMR (CDCl$_3$) δ1.62–1.98 (m, 8H, C$_5$H$_8$), 2.53 (d, J=7 Hz, 2H, CH$_2$), 3.80 (s, 3H, CH$_3$), 4.21 (t, J=7 Hz, 1H, OCH), 4.84–4.86 (m, 1H, NCH), 6.96–7.03 (m, 3H, Ar); $^{13}$C NMR (CDCl$_3$)δ26.33, 34.97, 49.78, 55.32, 58.48, 83.99, 114.99, 116.04, 121.63, 140.63, 149.12, 150.75, 182.87; Anal Calcd for C$_{15}$H$_{21}$NO$_4$: C, 64.50; H, 7.58; N, 5.01. Found: C, 64.54; H, 7.68; N, 4.93.

EXAMPLE 11

Methyl 3-amino-3-(3'-cyclopentoxy-4'-methoxyphenyl)propionate

To a stirred suspension of 3-amino-3-(3'-cyclopentyloxy-4'-methoxyphenyl)propionic acid (30 grams, 279 mmol) in methanol (150 mL) at 0° C., was added acetyl chloride (15.2 mL, 212 mmol) dropwise. After 15 minutes, the ice-water bath was removed. The resulting clear solution was stirred at room temperature for 2 h. The system was opened and the solvent was blown off with N$_2$ overnight. To the solid was added methanol (50 mL) and ether (300 mL). The resulting suspension was stirred at room temperature for 1 h. The suspension was filtered and the solid was washed with ether (100 mL). The solid was dissolved in a mixture of aqueous sodium carbonate (200 mL, sat), water (200 mL), and methylene chloride (250 mL). The organic layer was separated. The aqueous layer was extracted with methylene chloride (3×250 mL). The combined organic layers were dried over magnesium sulfate. Removal of solvent gave methyl 3-amino-3-(3'-cyclopentoxy-4'-methoxyphenyl) propionate as an oil (28.41 grams, 90% yield): $^1$H NMR (CDCl$_3$)δ1.56–1.97 (m, 10H, NH$_2$, C$_5$H$_8$), 2.62 (d, J=7 Hz, 2H, CH$_2$), 3.67 (s, 3H, CH$_3$), 3.81 (s, 3H, CH$_3$), 4.34 (t, J=6.8 Hz, 1H, CH), 4.74–4.79 (dd, J=5, 8.5 Hz, 1H, NCH), 6.78–6.90 (m, 3H, Ar); $^{13}$C NMR (CDCl$_3$)δ23.97, 32.76, 44.17, 51.58, 52.25, 56.07, 80.37, 111.96, 113.08, 119.08, 137.25, 147.72, 149.27, 172.49.

EXAMPLE 12

3-Amino-3-(3'-cyclopentyloxy-4'-methoxyphenyl)-1-propanol

To a stirred solid of sodium borohydride (37 grams, 978 mmol) at 0° C., was added methanol (50 mL). To this mixture at 0° C. was added a solution of methyl 3-amino-3-(3'-cyclopentyloxy-4'-methoxyphenyl)propionate (27 grams, 92.2 mmol) in methanol (500 mL) over 1 h. The mixture was stirred in that ice-water bath until the temperature of the reaction mixture stayed at 35° C. or lower for 30 minutes. (Caution: If the ice-water bath was removed too early, a highly exothermic reaction may occur.) The water bath was then removed and the solution was refluxed for 16 h. The solution was allowed to cool to room temperature. To the solution was added water (125 mL), followed by methylene chloride (250 mL) at 0° C. The resulting suspension was filtered. Half of the filtrate was removed in vacuo. The resulting solution was dissolved in methylene chloride (250 mL) and water (200 mL). The organic layer was separated. The aqueous layer was extracted with methylene chloride (3×250 mL). The combined organic layers were washed with brine (100 mL), and dried over magnesium sulfate. Removal of solvent gave an oil. The resulting oil was dried in vacuo to afford 3-amino-3-(3'-cyclopentyloxy-4'-methoxyphenyl)-1-propanol as a white solid (22.3 grams, 91% yield): mp, 216.0°–217.5° C.; $^1$H NMR (CDCl$_3$) δ1.52–1.68 (m, 2H, CH$_2$), 1.76–1.91 (m, 8H, C5H8), 2.92 (brs, 3H, NH$_2$, OH), 3.76 (t, J=5.5 Hz, 2H, CH$_2$), 3.82 (s, 3H, CH$_3$), 4.06 (t, J=Hz, 1H, OCH), 4.76–4.79 (m, 1H, NCH), 6.82–6.84 (m, 3H, Ar); $^{13}$C NMR (CDCl$_3$)δ23.96, 32.75, 39.91, 55.59, 56.10, 61.62, 80.46, 112.11, 112.99, 117.75, 138.65, 147.74, 149.12; Anal Calcd for C$_{15}$H$_{23}$NO$_3$0.05CH$_2$Cl$_2$: C, 67.05; H, 8.64, N, 5.20. Found: C, 67.02; H, 8.41; N, 5.08.

EXAMPLE 13

3-(3'-Cyclopentyloxy-4'-methoxyphenyl)-3-phthalimido-1-propanol

A mixture of 3-amino-3-(3'-cyclopentyloxy-4'methoxyphenyl)-1-propanol (4.31 grams, 16.24 mmol) and phthalic anhydride (2.41 grams, 16.27 mmol) was melted with a heat gun for 6 minutes. The mixture was allowed to cool to room temperature. Chromatography (silica gel 100 grams, 1:5 EtOAc:CH$_2$Cl$_2$) gave 3-(3'-cyclopentyloxy-4'-methoxyphenyl)-3-phthalimido-1-propanol as solid, (4.97 grams, 77% yield): mp, 59.0°–61.0° C.; $^1$H NMR (CDCl$_3$)δ1.56–1.98 (m, 9H, OH, C$_5$H$_8$), 2.48–2.59 (m, 1H, CHH), 2.71–2.83 (m, 1H, CHH), 3.66–3.74 (m, 2H, OCH$_2$), 3.80 (s, 3H, CH$_3$), 4.74–4.80 (m, 1H, CH), 5.51 (dd, J=6.5, 9.4 Hz, 1H, NCH), 6.78 (J=8.3 Hz, 1H, Ar), 7.05–7.09 (m, 1H, Ar), 7.16–7.17 (m, 1H, Ar), 7.64–7.70 (m, 2H, Ar), 7.75–7.81 (m, 2H, Ar); $^{13}$C NMR (CDCl$_3$)δ24.02, 32.71, 38.84, 51.44, 55.94, 59.75, 80.35, 111.58, 115.06, 120.54, 123.12, 131.60, 131.80, 133.86, 147.48, 149.55, 168.43; Anal Calcd for C$_{23}$H$_{25}$NO$_5$: C, 69.86; H, 6.37; N, 3.54. Found: C, 69.51; H, 6.41; N. 3.54.

EXAMPLE 14

3-(3'-Ethoxy-4'-methoxyphenyl)-3-(3"-nitro-phthalimido)-1-propanol

A mixture of 3-amino-3-(3'-ethoxy-4'-methoxyphenyl)-1-propanol (4.0 grams, 17.8 mmol) and 3-nitrophthalic anhydride (3.44 grams, 19.8 mmol) was melted with a heat gun for 6 minutes. The mixture was allowed to cool to room temperature. Chromatography (silica gel 80 grams, 1:5 EtOAc:CH$_2$Cl$_2$) gave 3-(3'-ethoxy-4'-methoxy)phenyl-3-(3"-nitro-phthalimido)-1-propanol as a yellow solid, (3.67 grams, 52% yield): mp, 143.0°–145.0° C.; $^1$H NMR (CDCl$_3$)δ1.47 (t, J=7Hz, 3H, CH$_3$), 1.48–1.52 (brs, 1H, OH), 2.51–2.62 (m, 1H, CHH), 2.72–2.84 (m, 1H, CHH), 3.69–3.73 (m, 2H, CH$_2$), 3.85 (s, 3H, CH$_3$), 4.12 (q, J=7 Hz, 2H, CH$_2$), 5.56 (dd, J=6.5, 9 Hz, 1H, NCH), 6.82 (d, J=8 Hz, 1H, Ar), 7.11–7.15 (m, 2H, Ar), 7.85–7.91 (m, 1H, Ar), 8.06–8.09 (m, 2H, Ar); $^{13}$C NMR (CDCl$_3$)δ14.71, 33.51, 52.61, 55.91, 59.87, 64.43, 111.26, 113.08, 120.91, 123.52, 126.91, 128.45, 130.82, 133.97, 135.21, 145.13, 148.27, 149.25, 163.02, 165.97; Anal Calcd for C$_{20}$H$_{20}$N$_2$O$_7$: C, 60.00; H, 5.03; N, 7.00. Found: C, 59.83; H, 4.97; N, 6.86.

EXAMPLE 15

3-(3"-Amino-phthalimido)-3-(3'-ethoxy-4'-methoxyphenyl)-1-propanol

A mixture of 3-(3'-ethoxy-4'-methoxyphenyl)-3-(3"-nitro-phthalimido)-1-propanol (600 mg, 1.5 mmol) and Pd/C (100 mg, 10%) in ethyl acetate (40 mL) was shaken under hydrogen (50 psi) for 16 h. The mixture was filtered through a pad of celite. Removal of solvent and chromatography (silica gel 80 grams, 1:3 EtOAc:CH$_2$Cl$_2$) gave 3-(3"-aminophthalimido)-3-(3'-ethoxy-4'-methoxyphenyl)-1-propanol as a yellow solid, (495 mg, 89% yield): mp, 81.0°–83.0° C.; $^1$H NMR (CDCl$_3$)δ1.45 (t, J=6.8 Hz, 3H, CH$_3$), 1.80 (brs., 1H, OH), 2.45–2.52 (m, 1H, CHH), 2.71–2.80 (m, 1H, CHH), 3.66–3.75 (m, 2H, OCH$_2$), 3.84 (s, 3H, CH$_3$), 4.09 (q, J=6.8 Hz, 2H, CH$_2$), 5.23 (br s, 2H, NH$_2$), 5.47 (dd, J=6.4, 9.8 Hz, 1H, CH), 6.78–6.83 (m, 2H, Ar), 7.07–7.13 (m, 3H, Ar), 7.33–7.39 (m, 1H, Ar); $^{13}$C NMR (CDCl$_3$)δ14.72, 33.92, 50.79, 55.87, 59.76, 64.34, 111.03, 111.14, 112.01, 113.07, 120.52, 121.60, 131.94, 132.49, 135.09, 145.24, 148.11, 148.84, 168.76, 170.31; Anal Calcd for C$_{20}$H$_{22}$N$_2$O$_5$: C, 64.85; H, 5.99; N, 7.56. Found: C, 64.44; H, 6.14; N, 6.88.

EXAMPLE 16

3-(3'-Ethoxy-4'-methoxyphenyl)-3-(3',4',5',6'-tetrahydrophthalimidoyl)-1-propanol A mixture of 3-amino-3-(3'-ethoxy-4'-methoxyphenyl)-1-propanol (4.0 grams, 17.76 mmol) and 3,4,5,6-tetrahydrophthalic anhydride (2.80 grams, 18.4 mmol) was melted with a heat gun for 6 minutes. The mixture was allowed to cool to room temperature. Chromatography (silica gel 150 grams, 1:3 EtOAc:CH$_2$Cl$_2$) gave 3-(3'-ethoxy-4'-methoxyphenyl)-3-(3',4',5',6'-tetrahydrophthalimidoyl)-1-propanol as an oil, (4.96 grams, 75% yield): $^1$H NMR (CDCl$_3$)δ1.45 (t,J=6.8 Hz, 3H, CH$_3$), 1.70–1.80 (m, 4H, CH$_2$CH$_2$), 1.91 (brs, 1H, OH), 2.27–2.32 (m, 4H, CH$_2$, CH$_2$), 2.41–2.58 (m, 1H, CHH), 2.61–2.68 (m, 1H, CHH), 3.59–3.65 (m, 2H, CH$_2$), 3.84 (s, 3H, CH$_3$), 4.09 (q, J=6.9 Hz, 2H, CH$_2$), 5.26 (dd, J=6.6, 9.5 Hz, 1H, NCH), 6.79 (d, J=8 Hz, 1H, Ar), 7.00–7.09 (m, 2H, Ar); $^{13}$C NMR (CDCl$_3$)δ14.64, 19.83, 21.19, 34.10, 50.90, 55.79, 59.69, 64.24, 111.04, 112.86, 120.41, 132.11, 141.28, 148.01, 148.73, 171.19; Anal Calcd for C$_{20}$H$_{25}$NO$_5$: C, 66.84; H, 7.01; N, 3.90. Found: C, 66.89; H, 6.84; N, 3.77.

EXAMPLE 17

3-(3',4'-Dimethoxyphenyl)-3-(1'-oxoisoindolinyl)-1-propanol

To a stirred suspension of 3-(3',4'-dimethoxyphenyl)-3-(1'-oxoisoindolinyl)propionic acid (3.74 grams, 10.96 mmol) in THF (60 mL) at −10°–15° C. (ice-salt bath), was added borane in THF (11 mL, 1M, 11 mmol). The suspension was allowed to warm to room temperature slowly overnight. To the resulting clear solution was added water (20 mL), followed by potassium carbonate (6 g). The organic layer was separated. The aqueous layer was extracted with methylene chloride (2×50 mL). The combined organic layers were washed with sodium carbonate (20 mL, sat), brine (20 mL), and dried over magnesium sulfate. Removal of solvent and chromatography (silica gel, 100 grams, 1:2, 1:1 EtOAc/CH$_2$Cl$_2$) gave 3-(3',4'-dimethoxyphenyl)-3-(1'-oxoisoindolinyl)-1-propanol as an oil, (2.52 grams, 70%). Ether (6 mL) and 2 drops of methanol were added to the oil. Hexane was added until the solution was turned cloudy. The mixture was stirred for 30 minutes to give a white solid and the solid was filtered: mp, 101.5°–103.0° C.; $^1$H NMR (CDCl$_3$)δ1.99–2.36 (m, 3H, CH$_2$, OH), 3.49–3.80 (m, 2H, OCH$_2$), 3.85 (s, 3H, CH$_3$), 3.89 (s, 3H, CH$_3$), 3.91 (d, J=17.2 Hz, 1H, CHH), 4.19 (d, J=17.2 Hz, 1H, CHH), 5.75 (dd, J=4, 11.5 Hz, 1H, NCH), 6.86–7.00(m, 3H, Ar), 7.27–7.56 (m, 3H, Ar), 7.86–7.89 (m, 1H, Ar); $^{13}$C NMR (CDCl$_3$)δ33.87, 46.22, 50.61, 55.91, 56.01, 58.55, 111.04, 111.73, 119.66, 122.81, 123.89, 128.64, 131.33, 131.56, 132.09, 141.35, 148.81, 148.24, 169.45; Anal Calcd for C$_{19}$H$_{21}$NO$_4$: C, 69.71; H, 6.47; N, 4.28. Found: C, 69.5I; H, 6.27; N, 4.12.

EXAMPLE 18

3-(3',4'-Dimethoxyphenyl)-1-methoxy-3-phthalimidopropane

To a solution of 3-(3',4'-dimethoxyphenyl)-3-phthalimido-1-propanol (1.02 grams, 2.99 mmol) and methyl iodide (0.37 mL, 5.94 mmol) in THF (10 mL) at room temperature, was added NaH (358 mg, 60%, 8.95 mmol). The mixture was stirred at room temperature for 45 minutes, and then was refluxed for 2 h. To the cooled mixture was added a few drops of NH$_4$Cl, then HCl (1N, 25 mL). The organic layer was separated. The aqueous layer was extracted with ethyl acetate (3×25 mL). The combined organic layers were washed with brine (25 mL), and dried over magnesium sulfate. Removal of solvent and chromatography (silica gel 100 grams, 1:5 EtOAc:hexane) gave 3-(3',4'-dimethoxyphenyl)-1-methoxy-3-phthalimidopropane as a white solid, (750 mg, 71% yield): mp, 91.5°–92.5° C.; $^1$H NMR (CDCl$_3$)δ2.50–2.59 (m, 1H, CHH), 2.70–2.86 (m, 1H, CHH), 3.27 (s, 3H, CH$_3$), 3.39 (t, J=6 Hz, 2H, CH$_2$), 3.85 (s, 3H, CH$_3$), 3.88 (s, 3H, CH$_3$), 5.49 (dd, J=6.8, 9.2 Hz, 1H, NCH), 6.81 (d, J=8 Hz, 1H, Ar), 7.11–7.15 (m, 2H, Ar), 7.67–7.72 (m, 2H, Ar), 7.77–7.83 (m, 2H, Ar); $^{13}$C NMR (CDCl$_3$)δ31.29, 51.93, 55.80, 58.69, 69.64, 110.84, 115.56, 120.62, 123.12, 131.90, 1332.03, 133.84, 148.58, 148.81, 168.38; Anal Calcd for C$_{20}$H$_{21}$NO$_5$: C, 67.59; H, 5.96; N, 3.94. Found: C, 67.54; H, 5.97; N, 3.84.

EXAMPLE 19

3-(3'-Ethoxy-4'-methoxyphenyl)-1-methoxy-3-phthalimidopropane

To a stirred mixture of sodium hydride (110 mg, 60%, 2.75 mmol) in THF (8 mL) at room temperature, was added iodomethane (0.54 grams, 3.78 mmol) followed by 3-(3'-ethoxy-4'-methoxyphenyl)-3-phthalimido-1-propanol (850 mg, 2.39 mmol). The mixture was stirred at room temperature for 15 h. To the mixture was added NH$_4$Cl (20 mL, sat). The organic layer was separated. The aqueous layer was extracted with methylene chloride (2×50 mL). The combined organic layers were washed with brine (50 mL) and dried over magnesium sulfate. Removal of solvent and chromatography (silica gel 200 grams, 1:12 EtOAc:CH$_2$Cl$_2$) gave 3-(3'-ethoxy-4'-methoxyphenyl)-1-methoxy-3-phthalimidopropane as an oil (360 mg, 41% yield). The resulting oil solidified after standing at room temperature over weekend: mp, 67.5°–70.0° C.; $^1$H NMR (CDCl$_3$)δ1.45 (t, J=7 Hz, 3H, CH$_3$), 2.50–2.60 (m, 1H, CHH), 2.71–2.85 (m, 1H, CHH), 3.26 (s, 3H, CH$_3$), 3.39 (t, J=6 Hz, 2H, CH$_2$), 3.84 (s, 3H, CH$_3$), 4.10 (q, J=7 Hz, 2H, CH$_2$), 5.47 (dd, J=7, 9.3 Hz, 1H, NCH), 6.81 (d, J=Hz, 1H, Ar), 7.09–7.16 (m, 2H, Ar), 7.66–7.69 (m, 2H, Ar), 7.76–7.82 (m, 2H, Ar). $^{13}$C NMR (CDCl$_3$)δ(APT) 14.67 (CH$_3$), 31.23 (CH$_2$), 51.89 (CH$_3$), 58.63 (CH), 64.25 (CH$_2$), 69.62 (CH$_2$), 111.13 (CH), 112.98 (CH), 120.58 (CH), 123.06 (CH), 131.87 (C), 131.92 (C), 133.78 (CH), 148.09 (C), 148.84 (C), 168.33 (C); Anal Calcd for C$_{21}$H$_{23}$NO$_5$·0.05H$_2$O: C, 67.66; H, 6.23; N, 3.75. Found: C, 67.91; H, 6.00; N, 3.71.

EXAMPLE 20

3-(3'-Cyclopentyloxy-4'-methoxyphenyl)-1-methoxy-3-phthalimidopropane

To a solution of 3-(3'-cyclopentyloxy-4'-methoxyphenyl)-3-phthalimido-1-propanol (786 mg, 1.99 mmol) and methyl iodide (0.25 mL, 4.0 mmol) in THF (1 0 mL) at room temperature, was added NaH (160 mg, 60%, 4.0 mmol). The mixture was stirred at room temperature for 1 h, and then was refluxed for 35 minutes. The mixture was allowed to cool to room temperature. To the resulting mixture was added a few drops of NH$_4$Cl, then HCl (1N, 25 mL). The organic layer was separated. The aqueous layer was extracted with ethyl acetate (3×30 mL). The combined organic layers were washed with brine (25 mL), and dried over Na$_2$SO$_4$. Removal of solvent and chromatography (silica gel 100 grams, 1:5 EtOAc:hexane) gave 3-(3'-cyclopentyloxy-4'-methoxyphenyl)-1-methoxy-3-phthalimidopropane as an oil, (510 mg, 63% yield). The oil solidified upon standing at room temperature to give a white solid: mp, 77.5°–80.0° C.; $^1$H NMR (CDCl$_3$)δ1.58–1.96 (m, 8H, C5H$_8$), 2.45–2.55 (m, 1H, CHH), 2.70–2.85 (m, 1H, CHH), 3.26 (s, 3H, CH$_3$), 3.39 (t, J=6 Hz, 2H, CH$_2$), 3.81 (s, 3H, CH$_3$), 4.78–4.80 (m, 1H, OCH), 5.46 (dd, J=7, 9.3 Hz, 1H, NCH), 6.79 (d, J=8.3 Hz, 1H, Ar), 7.06–7.10 (m, 1H, Ar), 7.17–7.26 (m, 1H, Ar), 7.67–7.69 (m, 2H, Ar), 7.78–7.82 (m, 2H, Ar); $^{13}$C NMR (CDCl$_3$)δ24.08, 31.30, 32.76, 51.94, 56.00, 58.71, 69.71, 80.37, 111.63, 115.09, 120.53, 123.12, 131.92, 131.96, 133.81, 147.53, 149.55, 169.37; Anal Calcd for C$_{24}$H$_{27}$NO$_5$: C, 70.40; H, 6.65; N, 3.42. Found: C, 70.32; H, 6.61; N, 3.31.

EXAMPLE 21

1-Ethoxy-3-(3'-ethoxy-4'-methoxyphenyl)-3-phthalimidopropane

To a stirred solution of 3-(3'-ethoxy-4'-methoxyphenyl)-3-phthalimido-1-propanol (1 gram, 2.82 mmol), ethyl bromide (0.42 mL, 5.63 mmol), and tetrabutyl ammonium iodide (200 mg, 0.54 mmol) in THF (10 mL) at room temperature, was added NaH (270 mg, 60%, 6.75 mmol). The mixture was stirred at room temperature for 45 minutes, and then was heated to reflux for 4 h. To the mixture was added a few drops of NH$_4$Cl, then HCl (1N, 25 mL). The organic layer was separated. The aqueous layer was extracted with ethyl acetate (3×25 mL). The combined organic layers were washed with brine (25 mL), and dried over magnesium sulfate. Removal of solvent and chromatography (silica gel 100 grams, 1:5 EtOAc:hexane) gave 1-ethoxy-3-(3'-ethoxy-4'-methoxyphenyl)-3-phthalimidopropane as an oil, (800 mg, 74% yield): $^1$H NMR (CDCl$_3$)δ1.06 (t, J=7Hz, 3H, CH$_3$), 1.46 (t, J=7 Hz, 3H, CH$_3$), 2.46–2.58 (m, 1H, CHH), 2.75–2.95 (m, 1H, CHH), 3.37 (q, J=7 Hz, 2H, CH$_2$), 3.44 (q, J=7 Hz, 2H, CH$_2$), 3.85 (s, 3H, CH$_3$), 4.12 (q, J=7 Hz, 2H, CH$_2$), 5.49 (dd, J=6.4, 9.5 Hz, 1H, NCH), 6.81 (d, J=8.2 Hz, 1H, Ar), 7.10–7.48 (m, 2H, Ar), 7.68–7.72 (m, 2H, Ar), 7.77–7.83 (m, 2H, Ar); $^{13}$C NMR (CDCl$_3$)δ14.73, 14.98, 31.31, 52.24, 55.89, 64.30, 66.33, 67.73, 111.11, 112.99, 120.61, 123.11, 132.00, 132.09, 133.80, 148.11, 148.84, 168.44; Anal Calcd for C$_{22}$H$_{25}$NO$_5$: C, 68.91; H, 6.57; N, 3.65. Found: C, 68.77; H, 6.47; N, 3.57.

EXAMPLE 22

1-Benzyloxy-3-(3'-ethoxy-4'-methoxyphenyl)-3-phthalimidopropane

To a stirred solution of 3-(3'-ethoxy-4'-methoxyphenyl)-3-phthalimido-1-propanol (680 mg, 1.92 mmol), benzyl bromide (0.46 mL, 3.86 mmol), and tetrabutyl ammonium iodide (80 mg, 0.21 mmol) in THF (20 mL) at room temperature, was added NaH (240 mg, 60%, 6.0 mmol). The mixture was stirred at room temperature for 15 h. To the mixture was added a few drops of NH$_4$Cl, then HCl (1N, 25 mL). The organic layer was separated. The aqueous layer was extracted with ethyl acetate (3×25 mL). The combined organic layers were washed with brine (25 mL), and dried over magnesium sulfate. Removal of solvent and chromatography (silica gel 100 grams, 1:5 EtOAc:hexane) gave 1-benzyloxy-3-(3'-ethoxy-4'-methoxyphenyl)-3-phthalimidopropane as an oil, (510 mg, 60% yield): $^1$H NMR (CDCl$_3$)δ1.46 (t, J=6.9 Hz, 3H, CH$_3$), 2.51–2.59 (m, 1H, CHH), 2.86–2.96 (m, 1H, CHH), 3.51 (t, J=5.5 Hz, CH$_2$), 3.85 (s, 3H, CH$_3$), 4.10 (q, J=7 Hz, CH$_2$), 4.43 (s, 2H, PhCH$_2$), 5.54 (dd, J=6.5, 9.5 Hz, 1H, NCH), 6.80 (d, J=8 Hz, 1H, Ar), 7.09–7.27 (m, 7H, Ar), 7.65–7.79 (m, 4H, Ar); $^{13}$C NMR (CDCl$_3$)δ14.73, 31.37, 52.12, 55.88, 64.29, 67.31, 73.10, 111.11, 112.95, 120.59, 123.09, 127.42, 127.62, 128.22, 131.92, 132.09, 133.77, 138.09, 148.12, 148.84, 168.42; Anal Calcd for C$_{27}$H$_{27}$NO$_5$: C, 72.79; H, 6.11; N, 3.14. Found: C, 72.66; H, 6.32; N, 3.16.

EXAMPLE 23

3-(3',4'-Dimethoxyphenyl)-1-ethoxy-3-(1'-oxoisoindolinyl)propane

To a stirred solution of 3-(3',4'-dimethoxyphenyl)-3-(1'-oxoisoindolinyl)-1-propanol (500 mg, 1.53 mmol), ethyl bromide (0.27 mL, 3.62 mmol) and tetrabutyl ammonium iodide (60 mg, 0.16 mmol) in THF (10 mL) at room temperature, was added NaH (160 mg, 60%, 4.0 mmol). The mixture was stirred at room temperature for 4 h. To the mixture was added NH$_4$Cl (20 mL, sat). The organic layer was separated. The aqueous layer was extracted with methylene chloride (2×25 mL). The combined organic layer was dried over magnesium sulfate. Removal of solvent and chromatography (silica gel 120 grams, 1:6 EtOAc:CH$_2$Cl$_2$) gave 3-(3',4'-dimethoxyphenyl)-1-ethoxy-3-(1'-oxoisoindolinyl)propane as an oil, (420 mg, 77% yield): $^1$H NMR (CDCl$_3$)δ1.09 (t, J=7 Hz, 3H, CH$_3$), 2.35–2.45 (m, 2H, CH$_2$), 3.35–3.58 (m, 4H, CH$_2$OCH$_2$), 3.84 (s, 3H, CH$_3$), 3.86 (s, 3H, CH$_3$), 4.00 (d, J=16.8 Hz, 1H, NCHH), 4.35 (d, d=16.8 Hz, 1H, NCHH), 5.66 (dd, J=6, 9.3 Hz, 1H, NCH), 6.82–6.98 (m, 3H, Ar), 7.35–7.53 (m, 3H, Ar), 7.84–7.88 (m, 1H, Ar); $^{13}$C NMR (CDCl$_3$)δ15.02, 31.62, 45.82, 51.51, 55.82, 55.90, 66.39, 67.86, 110.90, 111.27, 119.15, 122.68, 123.71, 127.86, 131.16, 132.28, 132.73, 141.28, 148.49, 149.08, 168.38; Anal Calcd for C$_{21}$H$_{25}$NO$_4$0.3H$_2$O: C, 69.90; H, 7.15; N, 3.88. Found: C, 69.69; H, 6.80; N, 3.73.

EXAMPLE 24

Tablets, each containing 50 milligrams of active ingredient, can be prepared in the following manner:

| Constituents (for 1000 tablets) | |
|---|---|
| active ingredient | 50.0 g |
| lactose | 50.7 g |
| wheat starch | 7.5 g |
| polyethylene glycol 6000 | 5.0 g |
| talc | 5.0 g |
| magnesium stearate | 1.8 g |
| demineralized water | q.s. |

The solid ingredients are first forced through a sieve of 0.6 mm mesh width. The active ingredient, the lactose, the talc, the magnesium stearate and half of the starch are then mixed. The other half of the starch is suspended in 40 milliliters of water and this suspension is added to a boiling solution of the polyethylene glycol in 100 milliliters of water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

EXAMPLE 25

Tablets, each containing 100 milligrams of active ingredient, can be prepared in the following manner:

| Constituents (for 1000 tablets) | |
|---|---|
| active ingredient | 100.0 g |
| lactose | 100.0 g |
| wheat starch | 47.0 g |
| magnesium stearate | 3.0 g |

All the solid ingredients are first forced through a sieve of 0.6 mm mesh width. The active ingredient, the lactose, the magnesium stearate and half of the starch then are mixed. The other half of the starch is suspended in 40 milliliters of water and this suspension is added to 100 milliliters of boiling water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

EXAMPLE 26

Tablets for chewing, each containing 75 milligrams of active ingredient, can be prepared in the following manner:

| Composition (for 1000 tablets) | |
|---|---|
| active ingredient | 75.0 g |
| mannitol | 230.0 g |
| lactose | 150.0 g |
| talc | 21.0 g |
| glycine | 12.5 g |
| stearic acid | 10.0 g |
| saccharin | 1.5 g |
| 5% gelatin solution | q.s. |

All the solid ingredients are first forced through a sieve of 0.25 mm mesh width. The mannitol and the lactose are mixed, granulated with the addition of gelatin solution, forced through a sieve of 2 mm mesh width, dried at 50° C. and again forced through a sieve of 1.7 mm mesh width. The active ingredient, the glycine and the saccharin are carefully mixed, the mannitol, the lactose granulate, the stearic acid and the talc are added and the whole is mixed thoroughly and compressed to form tablets of approximately 10 mm diameter which are concave on both sides and have a breaking groove on the upper side.

EXAMPLE 27

Tablets, each containing 10 milligrams of active ingredient, can be prepared in the following manner:

| Composition (for 1000 tablets) | |
|---|---|
| active ingredient | 10.0 g |
| lactose | 328.5 g |
| corn starch | 17.5 g |
| polyethylene glycol 6000 | 5.0 g |
| talc | 25.0 g |
| magnesium stearate | 4.0 g |
| demineralized water | q.s. |

The solid ingredients are first forced through a sieve of 0.6 mm mesh width. Then the active ingredient, lactose, talc, magnesium stearate and half of the starch are intimately mixed. The other half of the starch is suspended in 65 milliliters of water and this suspension is added to a boiling solution of the polyethylene glycol in 260 milliliters of water. The resulting paste is added to the pulverulent substances, and the whole is mixed and granulated, if necessary with the addition of water. The granulate is dried overnight at 35° C., forced through a sieve of 1.2 mm mesh width and compressed to form tablets of approximately 10 mm diameter which are concave on both sides and have a breaking notch on the upper side.

EXAMPLE 28

Gelatin dry-filled capsules, each containing 100 milligrams of active ingredient, can be prepared in the following manner:

| Composition (for 1000 capsules) | |
|---|---|
| active ingredient | 100.0 g |
| microcrystalline cellulose | 30.0 g |
| sodium lauryl sulphate | 2.0 g |
| magnesium stearate | 8.0 g |

The sodium lauryl sulphate is sieved into the active ingredient through a sieve of 0.2 mm mesh width and the two components are intimately mixed for 10 minutes. The microcrystalline cellulose is then added through a sieve of 0.9 mm mesh width and the whole is again intimately mixed for 10 minutes. Finally, the magnesium stearate is added through a sieve of 0.8 mm width and, after mixing for a further 3 minutes, the mixture is introduced in portions of 140 milligrams each into size 0 (elongated) gelatin dry-fill capsules.

EXAMPLE 29

A 0.2% injection or infusion solution can be prepared, for example, in the following manner:

| | |
|---|---|
| active ingredient | 5.0 g |
| sodium chloride | 22.5 g |
| phosphate buffer pH 7.4 | 300.0 g |
| demineralized water | to 2500.0 milliliters |

The active ingredient is dissolved in 1000 milliliters of water and filtered through a microfilter. The buffer solution is added and the whole is made up to 2500 milliliters with water. To prepare dosage unit forms, portions of 1.0 or 2.5 milliliters each are introduced into glass ampoules (each containing respectively 2.0 or 5.0 milligrams of active ingredient).

What is claimed is:
1. A compound having the formula:

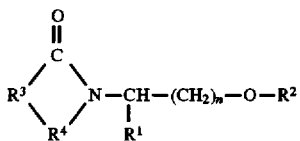

wherein $R^1$ is (i) straight, branched, or cyclic, unsubstituted alkyl of 1 to 12 carbon atoms; (ii) straight, branched, or cyclic, substituted alkyl of 1 to 12 carbon atoms; (iii) phenyl; or (iv) phenyl substituted with one or more substituents each selected independently of the other from the group consisting of nitro, cyano, trifluoromethyl, carbethoxy, carbomethoxy, carbopropoxy, acetyl, carbamoyl, acetoxy, carboxy, hydroxy, amino, acylamino, alkylamino, di(alkyl) amino, alkyl of 1 to 10 carbon atoms, cycloalkyl of 3 to 10 carbon atoms, bicycloalkyl of 5 to 12 carbon atoms, alkoxy of 1 to 10 carbon atoms, cycloalkoxy of 3 to 10 carbon atoms, bicycloalkoxy of 5 to 12 carbon atoms, and halo;

$R^2$ is hydrogen, alkyl of 1 to 8 carbon atoms, benzyl, pyridylmethyl, or alkoxymethyl;

$R^3$ is (i) ethylene, (ii) vinylene, (iii) a branched alkylene of 3 to 10 carbon atoms, (iv) a branched alkenylene of 3 to 10 carbon atoms, (v) cycloalkylene of 4 to 9 carbon atoms unsubstituted or substituted with one or more substituents each selected independently from the group consisting of nitro, cyano, trifluoromethyl, carbethoxy, carbomethoxy, carbopropoxy, acetyl, carbamoyl, acetoxy, carboxy, hydroxy, amino, amino substituted with alkyl of 1 to 6 carbon atoms, amino substituted with acyl of 1 to 6 carbon atoms, alkyl of 1 to 10 carbon atoms, alkoxy of 1 to 12 carbon atoms, and halo, (vi) cycloalkenylene of 4 to 9 carbon atoms unsubstituted or substituted with one or more substituents each selected independently from the group consisting of nitro, cyano, trifluoromethyl, carbethoxy, carbomethoxy, carbopropoxy, acetyl, carbamoyl, acetoxy, carboxy, hydroxy, amino, amino substituted with alkyl of 1 to 6 carbon atoms, amino substituted with acyl of 1 to 6 carbon atoms, alkyl of 1 to 10 carbon atoms, alkoxy of 1 to 12 carbon atoms, and halo, (vii) o-phenylene unsubstituted or substituted with one or more substituents each selected independently from the group consisting of nitro, cyano, trifluoromethyl, carbethoxy, carbomethoxy, carbopropoxy, acetyl, carbamoyl, acetoxy, carboxy, hydroxy, amino, amino substituted with alkyl of 1 to 6 carbon atoms, amino substituted with acyl of 1 to 6 carbon atoms, alkyl of 1 to 10 carbon atoms, alkoxy of 1 to 10 carbon atoms, or halo, (viii) naphthyl, or (ix) pyridyl;

$R^4$ is —CX—, —CH$_2$— or —CH$_2$CX—;

X is O or S; and, n is 0, 1, 2, or 3.

2. A compound according to claim 1 wherein $R^1$ is (i) straight, branched, or cyclic, unsubstituted alkyll of 1 to 12 carbon atoms; (ii) straight, branched, or cyclic, substituted alkyl of 1 to 12 carbon atoms; (iii) phenyl; or (iv) phenyl substituted with one or more substituents each selected independently of the other from the group consisting of nitro, cyano, trifluoromethyl, carbethoxy, carbomethoxy, carbopropoxy, acetyl, carbamoyl, acetoxy, carboxy, hydroxy, amino, substituted amino, alkyl of 1 to 10 carbon atoms, alkoxy of 1 to 10 carbon atoms, or halo;

$R^2$ is hydrogen or alkyl of 1 to 8 carbon atoms;

$R^3$ is (i) ethylene, (ii) vinylene, (iii) a branched alkylene of 3 to 10 carbon atoms, (iv) a branched alkenylene of 3 to 10 carbon atoms, (v) cycloalkylene of 4 to 9 carbon atoms unsubstituted or substituted with one or more substituents each selected independently from the group consisting of nitro, cyano, trifluoromethyl, carbethoxy, carbomethoxy, carbopropoxy, acetyl, carbamoyl, acetoxy, carboxy, hydroxy, amino, amino substituted with alkyl of 1 to 4 carbon atoms, alkoxy of 1 to 4 carbon atoms, and halo, (vi) cycloalkenylene of 4 to 9 carbon atoms unsubstituted or substituted with one or more substituents each selected independently from the group consisting of nitro, cyano, trifluoromethyl, carbethoxy, carbomethoxy, carbopropoxy, acetyl, carbamoyl, acetoxy, carboxy, hydroxy, amino, amino substituted with alkyl of 1 to 4 carbon atoms, alkoxy of 1 to 4 carbon atoms, and halo, or (vii) o-phenylene unsubstituted or substituted with one or more substituents each selected independently from the group consisting of nitro, cyano, trifluoromethyl, carbethoxy, carbomethoxy, carbopropoxy, acetyl, carbamoyl, acetoxy, carboxy, hydroxy, amino, amino substituted with alkyl of 1 to 4 carbon atoms, alkoxy of 1 to 4 carbon atoms, and halo; and $R^4$ is —CX— or —CH$_2$—.

3. A compound claim 2 wherein $R^4$ is —CO— and $R^1$ is 3,4-diethoxyphenyl.

4. A compound of claim 2 wherein $R^4$ is —CO— and $R^1$ is 3-ethoxy-4-methoxyphenyl.

5. A compound of claim 2 wherein $R^4$ is —CO— and $R^1$ is 3-cyclopentoxy-4-methoxyphenyl.

6. A compound of claim 2 wherein $R^1$ is 3,4-dimethoxyphenyl.

7. A compound of claim 2 wherein $R^1$ is 3-ethoxy-4-methoxyphenyl.

8. A compound of claim 2 wherein $R^1$ is 3-isopropoxy-4-methoxyphenyl.

9. A compound of claim 2 wherein $R^1$ is 3-cyclopentoxy-4-methoxyphenyl.

10. A compound of claim 2 wherein $R^1$ is 3-ethoxy-4-ethylphenyl.

11. A compound of claim 2 wherein $R^4$ is —CO— and $R^1$ is substituted phenyl.

12. A compound of claim 2 wherein $R^4$ is —CH$_2$— and $R^1$ is substituted phenyl.

13. A compound of claim 2 wherein $R^4$ is —CH$_2$CO— and $R^1$ is substituted phenyl.

14. The method of reducing levels of TNF$_\alpha$ in a mammal which comprises administering thereto an effective amount of a compound of claim 1.

15. The method of reducing levels of TNF$_\alpha$ in a mammal which comprises administering thereto an effective amount of a compound of the formula:

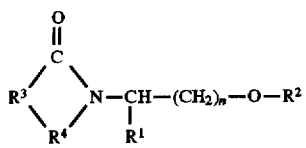

wherein

R¹ is (i) straight, branched, or cyclic, unsubstituted alkyl of 1 to 12 carbon atoms; (ii) straight, branched, or cyclic, substituted alkyl of 1 to 12 carbon atoms; (iii) phenyl; or (iv) phenyl substituted with one or more substituents each selected independently of the other from the group consisting of nitro, cyano, trifluoromethyl, carbethoxy, carbomethoxy, carbopropoxy, acetyl, carbamoyl, acetoxy, carboxy, hydroxy, amino, substituted amino, acylamino, alkyl (dialkyl)amino, alkyl of 1 to 10 carbon atoms, cycloalkyl of 3 to 10 carbon atoms, bicycloalkyl of 5 to 12 carbon atoms, alkoxy of 1 to 10 carbon atoms, cycloalkoxy of 3 to 10 carbon atoms, bicycloalkoxy of 5 to 12 carbon atoms, or halo;

R² is —H, alkyl of 1 to 8 carbon atoms, benzy, pyridylmethyl, or alkoxymethyl;

R³ is i) ethylene, ii) vinylene, iii) a branched alkylene of 3 to 10 carbon atoms, iv) a branched alkenylene of 3 to 10 carbon atoms, v) cycloalkylene of 4 to 9 carbon atoms unsubstituted or substituted with 1 or more substituents each selected independently from nitro, cyano, trifluoromethyl, carbethoxy, carbomethoxy, carbopropoxy, acetyl, carbamoyl, acetoxy, carboxy, hydroxy, amino, substituted amino alkyl of 1 to 6 carbon atoms, substituted amino acyl of 1 to 6 carbon atoms, alkyl of 1 to 10 carbon atoms, alkoxy of 1 to 12 carbon atoms, or halo, vi) cycloalkenylene of 4 to 9 carbon atoms unsubstituted or substituted with 1 or more substituents each selected independently from nitro, cyano, trifluoromethyl, carbethoxy, carbomethoxy, carbopropoxy, acetyl, carbamoyl, acetoxy, carboxy, hydroxy, amino, substituted amino alkyl of 1 to 6 carbon atoms, substituted amino acyl of 1 to 6 carbon atoms, alkyl of 1 to 10 carbon atoms, alkoxy of 1 to 12 carbon atoms, or halo, vii) o-phenylene unsubstituted or substituted with 1 or more substituents each selected independently from nitro, cyano, trifluoromethyl, carbethoxy, carbomethoxy, carbopropoxy, acetyl, carbamoyl, acetoxy, carboxy, hydroxy, amino, substituted amino alkyl of 1 to 6 carbon atoms, substituted amino acyl of 1 to 6 carbon atoms, alkyl of 1 to 10 carbon atoms, alkoxy of 1 to 12 carbon atoms, or halo, viii) napthyl, or ix) pyridyl;

R⁴ is —CX—, —CH₂— or —CH₂CX—;

X is O or S; and, n is 0, 1, 2, or 3.

16. The method of inhibiting TNFα-activated retrovirus replication in a mammal which comprises administering thereto an effective amount of a compound according to claim 1.

17. A pharmaceutical composition comprising an amount of a compound according to claim 1 effective upon single or multiple dosage to inhibit TNFα and a pharmaceutically acceptable carrier.

18. A pharmaceutical composition comprising an amount of a compound according to claim 2 effective upon single or multiple dosage to inhibit TNFα and a pharmaceutically acceptable carrier.

19. The method of inhibiting phosphodiesterases in a mammal which comprises administering thereto an effective amount of a compound of the formula:

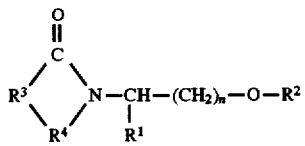

wherein

R¹ is (i) straight, branched, or cyclic, unsubstituted alkyl of 1 to 12 carbon atoms; (ii) straight, branched, or cyclic, substituted alkyl of 1 to 12 carbon atoms; (iii) phenyl; or (iv) phenyl substituted with one or more substituents each selected independently of the other from the group consisting of nitro, cyano, trifluoromethyl, carbethoxy, carbomethoxy, carbopropoxy, acetyl, carbamoyl, acetoxy, carboxy, hydroxy, amino, substituted amino, acylamino, alkyl (dialkyl)amino, alkyl of 1 to 10 carbon atoms, cycloalkyl of 3 to 10 carbon atoms, bicycloalkyl of 5 to 12 carbon atoms, alkoxy of 1 to 10 carbon atoms, cycloalkoxy of 3 to 10 carbon atoms, bicycloalkoxy of 5 to 12 carbon atoms, or halo;

R² is —H, alkyl of 1 to 8 carbon atoms, benzy, pyridylmethyl, or alkoxymethyl;

R³ is i) ethylene, ii) vinylene, iii) a branched alkylene of 3 to 10 carbon atoms, iv) a branched alkenylene of 3 to 10 carbon atoms, v) cycloalkylene of 4 to 9 carbon atoms unsubstituted or substituted with 1 or more substituents each selected independently from nitro, cyano, trifluoromethyl, carbethoxy, carbomethoxy, carbopropoxy, acetyl, carbamoyl, acetoxy, carboxy, hydroxy, amino, substituted amino alkyl of 1 to 6 carbon atoms, substituted amino acyl of 1 to 6 carbon atoms, alkyl of 1 to 10 carbon atoms, alkoxy of 1 to 12 carbon atoms, or halo, vi) cycloalkenylene of 4 to 9 carbon atoms unsubstituted or substituted with 1 or more substituents each selected independently from nitro, cyano, trifluoromethyl, carbethoxy, carbomethoxy, carbopropoxy, acetyl, carbamoyl, acetoxy, carboxy, hydroxy, amino, substituted amino alkyl of 1 to 6 carbon atoms, substituted amino acyl of 1 to 6 carbon atoms, alkyl of 1 to 10 carbon atoms, alkoxy of 1 to 12 carbon atoms, or halo, vii) o-phenylene unsubstituted or substituted with 1 or more substituents each selected independently from nitro, cyano, trifluoromethyl, carbethoxy, carbomethoxy, carbopropoxy, acetyl, carbamoyl, acetoxy, carboxy, hydroxy, amino, substituted amino alkyl of 1 to 6 carbon atoms, substituted amino acyl of 1 to 6 carbon atoms, alkyl of 1 to 10 carbon atoms, alkoxy of 1 to 12 carbon atoms, or halo, viii) napthyl, or ix) pyridyl;

R⁴ is —CX—, —CH₂— or —CH₂CX—;

X is O or S; and n is 0, 1, 2, or 3.

20. A compound according to claim 19 which is 3-phthimido-3-(3,4-dimethoxy-phenyl)propan-1-ol; 2-phthimidodo-2-(3,4-dimethoxyphenyl)ethanol; 3-phthalimido-3-(3,4-diethoxyphenyl)propan-1-ol; 3-phthalimido-3-(3,4-dimethoxyphenyl)-1-methoxypropane; 2-phthalimido-2-(3,4-dimethoxyphenyl)-1-methoxyethane; 3-phthalimido-3-(3,4-diethoxyphenyl)-1-methoxypropane; 3-phthalimido-3-(3,4-dimethoxyphenyl)-

1-ethoxypropane; 3-phthalimido-3-(3,4-dimethoxyphenyl)-1-(3-pyridylmethoxy)propane; 3-phthalimido-3-(3,4-diethoxyphenyl)-1-(3-pyridylmethoxyl)propane; 3-phthalimido-3-naphthylpropan-1-ol; 3-phthalimido-3-(3,4-diethylphenyl)propan-1-ol; 3-phthalimido-3-(3,4-dipropylphenyl)propan-1-ol; 3-phthimido-3-(3,4-diethylphenyl)-1-methoxypropane; 3-phthalimido-3-(3,4-diethoxyphenyl)-1-ethoxypropane; 3-phthalimido-3-cyclohexyl-1-methoxypropane-, 3-phthalimido-3-(3,4-diethylcyclohexyl)-1-methoxypropane; 3-(1-oxoisoindolinyl)-3-(3,4-dimethoxyphenyl)propan-1-ol; 2-(1-oxoisoindolinyl)-2-(3,4-di-methoxyphenyl)ethanol; 3-(1-oxoisoindolinyl)-3-(3,4-diethoxyphenyl)propan-1-ol; 3-(1-oxoisoindolinyl-3-(3,4-dimethoxyphenyl)-1-methoxypropane; 2-(1-oxoisoindolinyl)-2-(3,4-dimethoxyphenyl)-1-methoxyethane; 3-(1-oxoisoindolinyl)-3-(3,4-diethoxyphenyl)-1-methoxypropane; 3-(1-oxoisoindolinyl)-3-(3,4-dimethoxyphenyl)-1-ethoxypropane; 3-(1-oxoisoindolinyl)-3-(3,4-dimethoxyphenyl)-1-(3-pyridylmethoxy)propane; 3-(1-oxoisoindolinyl)-3-(3,4-diethoxyphenyl)-1-(3-pyridylmethoxyl)propane; 3-(1-oxoisoindolinyl)-3-naphthylpropan-1-ol; 3-(1-oxoisoindolinyl)-3-(3,4-diethylphenyl)propan-1-ol; 3-(1-oxoisoindolinyl)-3-(3,4-dipropylphenyl)propan-1-ol; 3-(1-oxoisoindolinyl)-3-(3,4-diethylphenyl)-1-methoxypropane; or 3-(1-oxoisoindolinyl)-3-(3,4-diethoxyphenyl)-1-ethoxypropane.

\* \* \* \* \*